US010905343B2

(12) United States Patent
Fung et al.

(10) Patent No.: US 10,905,343 B2
(45) Date of Patent: Feb. 2, 2021

(54) PERCEPTION CHANGE-BASED ADJUSTMENTS IN HEARING PROSTHESES

(71) Applicant: Cochlear Limited, Macquarie University (AU)

(72) Inventors: Stephen Fung, Dundas Valley (AU); Alex von Brasch, Cremorne (AU); Kieran Reed, Eastwood (AU)

(73) Assignee: COCHLEAR LIMITED, Macquarie University (AU)

( * ) Notice: Subject to any disclaimer, the term of this patent is extended or adjusted under 35 U.S.C. 154(b) by 80 days.

(21) Appl. No.: 16/215,828

(22) Filed: Dec. 11, 2018

(65) Prior Publication Data

US 2019/0104957 A1    Apr. 11, 2019

Related U.S. Application Data

(62) Division of application No. 15/278,464, filed on Sep. 28, 2016, now Pat. No. 10,194,814.

(51) Int. Cl.
| | |
|---|---|
| *A61B 5/04* | (2006.01) |
| *A61N 1/36* | (2006.01) |
| *H04R 25/00* | (2006.01) |
| *A61B 5/12* | (2006.01) |
| *A61N 1/05* | (2006.01) |

(52) U.S. Cl.
CPC .......... *A61B 5/04001* (2013.01); *A61B 5/125* (2013.01); *A61N 1/0541* (2013.01); *A61N 1/36036* (2017.08); *A61N 1/36038* (2017.08); *H04R 25/505* (2013.01); *H04R 25/70* (2013.01); *H04R 25/554* (2013.01)

(58) Field of Classification Search
CPC ................ A61B 5/04001; A61B 5/125; A61N 1/36038; A61N 1/36036; A61N 1/0541
See application file for complete search history.

(56) References Cited

U.S. PATENT DOCUMENTS

| | | |
|---|---|---|
| 8,086,319 B2 | 12/2011 | van Dijk |
| 8,265,765 B2 | 9/2012 | Nicolai et al. |
| (Continued) | | |

FOREIGN PATENT DOCUMENTS

WO    2007/134048 A2    11/2007

OTHER PUBLICATIONS

International Search Report and Written Opinion in corresponding International Application No. PCT/IB2017/055801, dated Jan. 11, 2018, 11 pages.

(Continued)

*Primary Examiner* — Catherine M Voorhees
*Assistant Examiner* — Roland Dinga
(74) *Attorney, Agent, or Firm* — Edell, Shapiro & Finnan, LLC

(57) ABSTRACT

Presented herein are substantially automated techniques that enable an electro-acoustic or other hearing prosthesis implanted in a recipient to use objective measurements to determine when the recipient is likely experiencing sound perception changes. Once one or more perception changes are detected, the hearing prosthesis may initiate one or more remedial actions to, for example, address the perception changes. As described further below, the one or more remedial actions may include adjustments to the recipient's operational map to reverse the one or more perception changes.

20 Claims, 7 Drawing Sheets

(56) References Cited

U.S. PATENT DOCUMENTS

| | | |
|---|---|---|
| 9,155,886 B2 | 10/2015 | James et al. |
| 2012/0265270 A1 | 10/2012 | Cornejo Cruz et al. |
| 2012/0290045 A1 | 11/2012 | Nicolai et al. |
| 2013/0282077 A1 | 10/2013 | Saoji et al. |
| 2014/0275730 A1 | 9/2014 | Lievens et al. |
| 2015/0057714 A1 | 2/2015 | Litvak et al. |
| 2015/0237452 A1 | 8/2015 | Vanpoucke |
| 2015/0335890 A1 | 11/2015 | Fredelake |
| 2017/0208403 A1* | 7/2017 | Nakajima ............ H01L 41/193 |
| 2017/0347213 A1* | 11/2017 | Goorevich ............ H04R 25/43 |
| 2017/0359661 A1* | 12/2017 | Goorevich ........... H04R 25/356 |
| 2018/0015287 A1* | 1/2018 | Heasman ........... A61N 1/36039 |

OTHER PUBLICATIONS

Extended European Search Report received in related application No. EP17855101, dated Apr. 1, 2020 (7 pages).

* cited by examiner

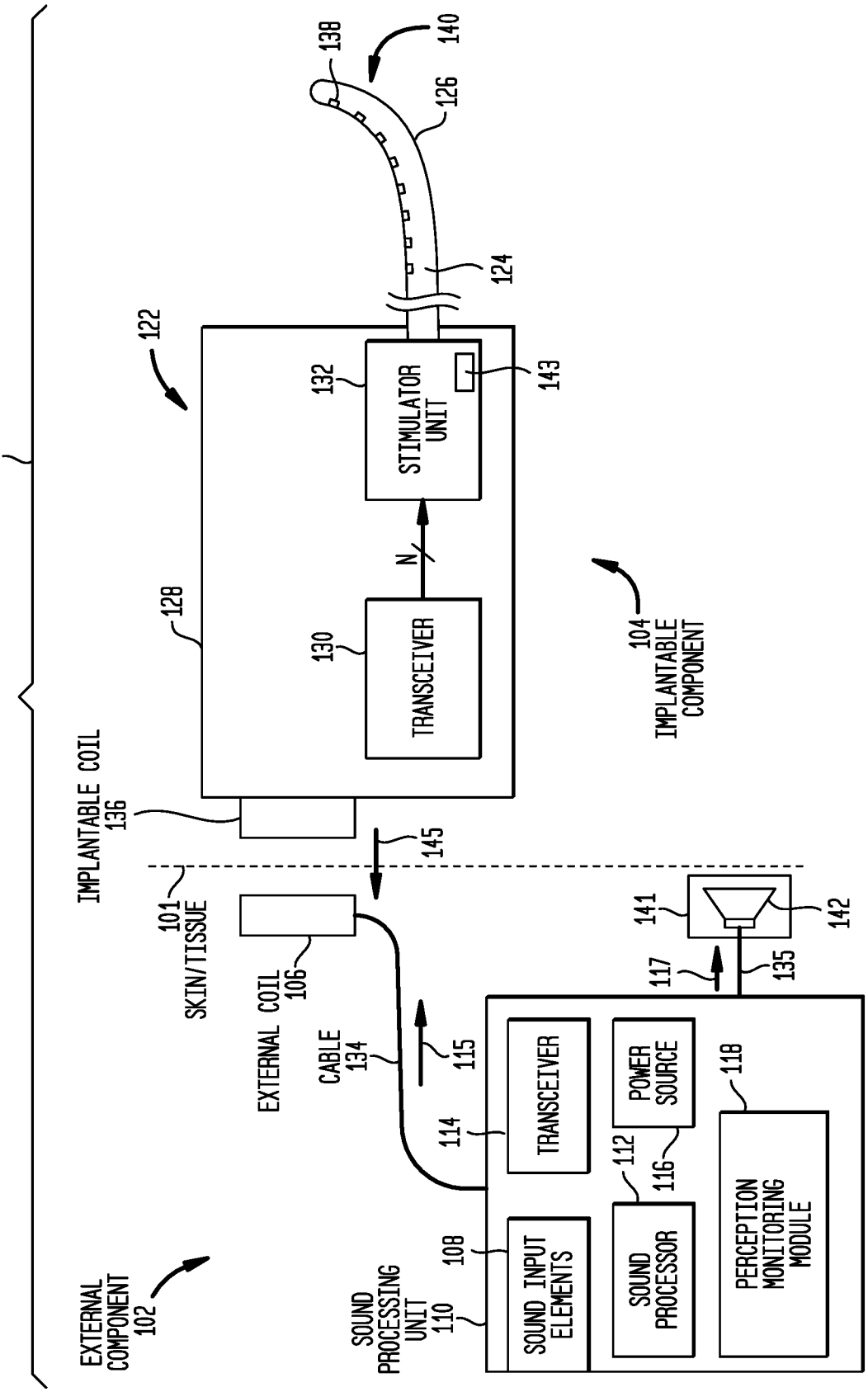

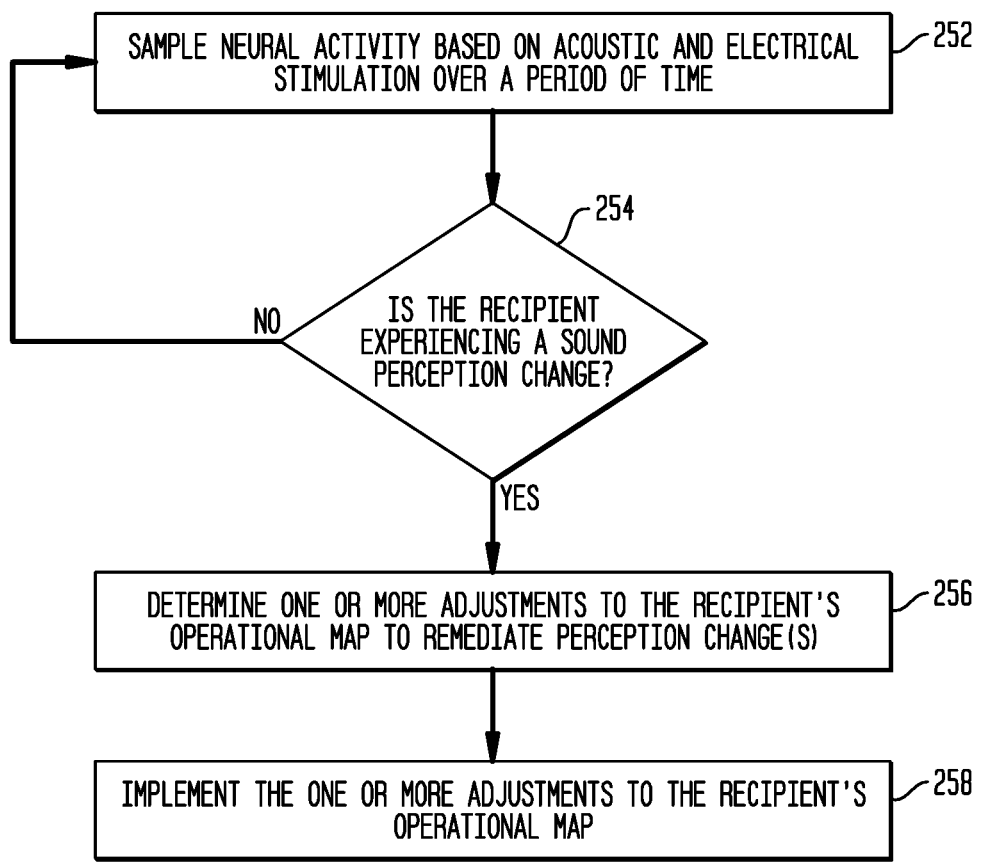

PERCEPTION CHANGE-BASED ADJUSTMENTS IN HEARING PROSTHESES

CROSS-REFERENCE TO RELATED APPLICATIONS

This a divisional application of U.S. patent application Ser. No. 15/278,464, filed on Sep. 28, 2016, the content of which hereby incorporated by reference herein.

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: sampling neural activity in response to acoustic stimulation signals and electrical stimulation signals delivered by an electro-acoustic hearing prosthesis worn by a recipient; analyzing the sampled neural activity to determine that the recipient has experienced a sound perception change; and adjusting, based on the sound perception change experienced by the recipient, one or more operations of the electro-acoustic hearing prosthesis to remediate the sound perception change.

In another aspect, a method is provided. The method comprises: obtaining inner ear responses evoked by stimulation signals at a hearing prosthesis worn by a recipient; objectively identifying, based on an analysis of the obtained inner ear responses, one or more changes in the recipient's perception of sound signals relative to a predetermined perception of sound signals; and adjusting operation of the hearing prosthesis to reverse the one or more changes in a recipient's perception of sound signals.

In another aspect, a hearing prosthesis is provided. The hearing prosthesis comprises: an intra-cochlear stimulating assembly configured to be implanted in a recipient, wherein the intra-cochlear stimulating assembly comprises a plurality of stimulating contacts configured to deliver electrical stimulation signals to the recipient; an acoustic receiver configured to deliver acoustic stimulation signals to the recipient; and one or more processors configured to: sample, via one or more of the stimulating contacts, neural activity of the recipient in response to measurement stimulation signals delivered by the hearing prosthesis, analyze the sampled neural activity to determine that the recipient has experienced a sound perception change, and adjust, based on the sound perception change experienced by the recipient, one or more settings of the electro-acoustic hearing prosthesis used to convert sound signals into the acoustic stimulation signals or the electrical stimulation signals, wherein the one or more settings are adjusted to restore the recipient's sound perception to a predetermined sound perception.

BRIEF DESCRIPTION OF THE DRAWINGS

Embodiments of the present invention are described herein in conjunction with the accompanying drawings, in which:

FIG. 1B is a block diagram of the electro-acoustic hearing prosthesis of FIG. 1A;

FIG. 2A is a flowchart of a method in accordance with embodiments presented herein;

mist

DETAILED DESCRIPTION

Figure 1A:
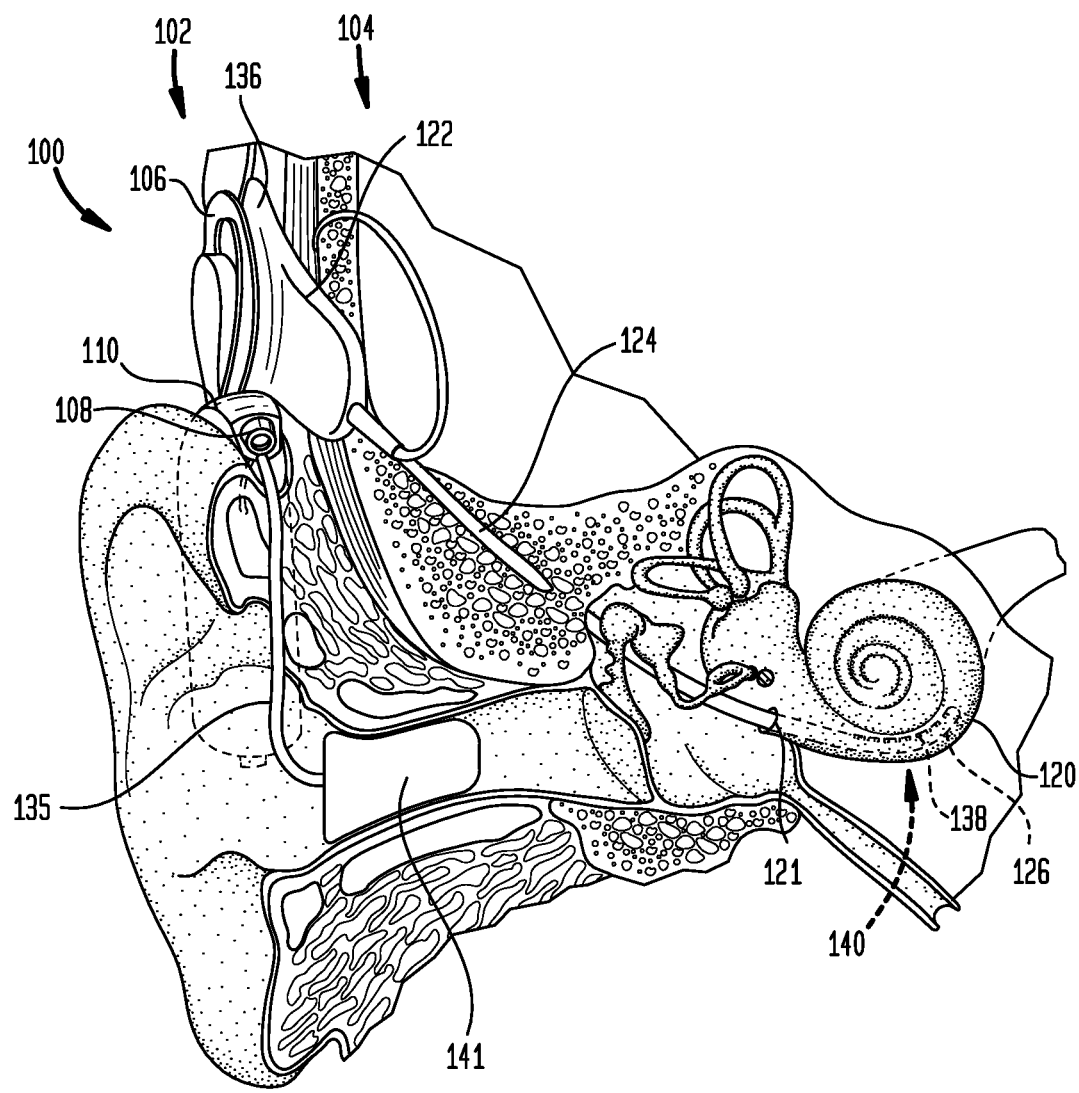
FIG. 1A is a schematic diagram illustrating an electro-acoustic hearing prosthesis in accordance with embodiments presented herein.

Auditory/hearing prosthesis recipients suffer from different types of hearing loss (e.g., conductive and/or sensorineural) and/or different degrees/severity of hearing loss. However, it is now common for many hearing prosthesis recipients to retain some residual natural hearing ability (residual hearing) after receiving the hearing prosthesis. For example, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the lower frequency regions of the cochlea.

Due, at least in part, to the ability to preserve residual hearing, the number of recipients who are candidates for different types of implantable hearing prostheses, particularly electro-acoustic hearing prostheses, has continued to expand. Electro-acoustic hearing prostheses are medical devices that deliver both acoustic stimulation (i.e., acoustic stimulation signals) and electrical stimulation (i.e., electrical stimulation signals), possibly simultaneously, to the same ear of a recipient. Typically, due to the limits of residual hearing in the implanted ear, the acoustic stimulation is used to present sound signal components corresponding to the lower frequencies of input sound signals (as determined from the residual hearing capabilities of the implanted ear), while the electrical stimulation is used to present sound signal components corresponding to the higher frequencies. The tonotopic region of the cochlea where the sound or stimulation output transitions from the acoustic stimulation to the electrical stimulation is called the cross-over frequency region.

Recipients of electro-acoustic hearing prostheses typically benefit from having the acoustic stimulation in addition to the electrical stimulation, as the acoustic stimulation adds a more "natural" sound to their hearing perception over the electrical stimulation signals only in that ear. The addition of the acoustic stimulation can, in some cases, also provide improved pitch and music perception and/or appreciation, as the acoustic signals may contain a more salient lower frequency (e.g., fundamental pitch, F0) representation than is possible with electrical stimulation. Other benefits of electro-acoustic hearing prosthesis may include, for example, improved sound localization, binaural release from unmasking, the ability to distinguish acoustic signals in a noisy environment, etc.

The effectiveness of electro-acoustic and other hearing prostheses generally depends on how well a particular prosthesis is configured or "fitted" to the recipient of the particular prosthesis. For instance, the "fitting" of a hearing prosthesis to a recipient, sometimes also referred to as "programming" or "mapping," creates a set of configuration settings, parameters, and other data (collectively and generally "settings" herein) that define the specific operational characteristics of the hearing prosthesis. In the case of electro-acoustic hearing prostheses, fitting determines how the prosthesis operates to convert portions (frequencies and/or frequency ranges) of detected sound signals (sounds) into electrical and acoustic stimulation signals. In particular, the fitting process is used to determine the output levels (e.g., acoustic levels for acoustic simulation and current levels for electrical stimulation), which includes a mapping of received sound signal levels to these various output levels. In addition, the fitting process for an electro-acoustic hearing prosthesis is used to determine the "cross-over frequency," which is the frequency/frequency-range where the stimulation output transitions from acoustic stimulation to electrical stimulation. Collectively, the various settings determined for a recipient during a fitting process are referred to herein as the recipient's "operational program" or "operational map" and will dictate how the electro-acoustic hearing prosthesis operates to convert sound signals into acoustic and/or electrical stimulation.

After being fitted with an electro-acoustic hearing prosthesis, a recipient's hearing abilities (e.g., residual hearing) can change over time. For example, a recipient's residual hearing may gradually decay as he/she ages, a recipient's residual hearing may rapidly deteriorate in response to disease or trauma, etc. When the recipient's hearing abilities change, the recipient's current operational map may be inadequate to represent the sound signals in a manner such that they can be properly perceived/understood by the recipient. In other words, as the recipient's hearing abilities change, the recipient may begin to incorrectly perceive various parts of sound signals due to the fact that the operational map of the hearing prosthesis does not account for the hearing ability changes experienced by the recipient. In certain cases, a recipient may notice these sound "perception changes" and contact a hearing professional (e.g., clinician, audiologist, etc.) to conduct a new fitting process to update the operational map.

In other cases, a recipient may be unable to detect the perception changes on his/her own. For example, young children, new prosthesis recipients, etc., may have substantial difficulty in determining when a perception change occurs. In conventional arrangements, the perception change can only be detected within a clinical environment, typically using complex equipment and techniques implemented by trained hearing professionals. However, recipients generally do not visit clinics on a regular basis due to, for example, high costs, low availability of trained audiologists, etc. Therefore, the need to visit a clinic in order to detect a perception change may not only be cost prohibitive for certain recipients, but may also require the recipient to live with the perception change (possibly unknowingly) for a significant period of time before the perception change is identified, let alone addressed. A perception change that exist for extended periods of time can lead to negative learning outcomes where the recipient "learns" to perceive certain words, phonemes, or other sounds incorrectly. In cases where a recipient experiences negative learning outcomes, particularly for extended periods of time, the recipient may have difficulty re-learning to properly perceive/understand the sounds that have been "learned" incorrectly.

Presented herein are substantially automated techniques that enable an electro-acoustic or other hearing prosthesis implanted in a recipient to use objective measurements to determine when the recipient is likely experiencing sound perception changes. The use of objective measurements, rather than subjective measurements, to detect sound perception changes does not require the recipient to actively participate in the detection of the sound perception change. Additionally, the techniques are substantially integrated into the hearing prosthesis and can be performed outside of the clinic setting/environment. As a result, sound perception changes can be detected more rapidly than in conventional arrangements. Once one or more perception changes are detected, the hearing prosthesis may initiate one or more remedial actions to, for example, address the perception changes. As described further below, the one or more corrective actions may include adjustments to the recipient's operational map to reverse the one or more perception changes.

For ease of illustration, embodiments are primarily described herein with reference to one specific type of hearing prosthesis, namely an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.), etc.

FIG. 1A is schematic diagram of an exemplary electro-acoustic hearing prosthesis 100 configured to implement embodiments of the present invention, while FIG. 1B is a block diagram of the electro-acoustic hearing prosthesis. The electro-acoustic hearing prosthesis 100 includes an external component 102 and an internal/implantable component 104.

The external component 102 is directly or indirectly attached to the body of the recipient and comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc.), a sound processor 112, an external transceiver unit (transceiver) 114, a power source 116, and a perception monitoring module 118. The sound processing unit 110 may be, for example, a behind-the-ear (BTE) sound processing unit, a body-worn sound processing unit, a button sound processing unit, etc.

Connected to the sound processing unit 110 via a cable 135 is a hearing aid component 141. The hearing aid component 141 includes a receiver 142 (FIG. 1B) that may be, for example, positioned in or near the recipient's outer ear. The receiver 142 is an acoustic transducer that is configured to deliver acoustic signals (acoustic stimulation signals) to the recipient via the recipient's ear canal and middle ear.

FIGS. 1A and 1B illustrate the use of a receiver 142 to deliver acoustic stimulation to the recipient. However, it is to be appreciated that other types of devices may be used in other embodiments to deliver the acoustic stimulation. For example, other embodiments may include an external or implanted vibrator that is configured to deliver acoustic stimulation to the recipient.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 and includes a plurality of longitudinally spaced intra-cochlear electrical stimulating contacts (electrodes) 138 that collectively form a contact array 140 for delivery of electrical stimulation (current) to the recipient's cochlea. In certain arrangements, the contact array 140 may include other types of stimulating contacts, such as optical stimulating contacts, in addition to the electrodes 138.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical output signals therefrom. The sound processor 112 is configured execute sound processing and coding to convert the output signals received from the sound input elements into coded data signals that represent acoustical and/or electrical stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustic stimulation signals to the recipient. As such, depending on the current operational map, the sound processor 112 is configured to convert the output signals received from the sound input elements into a first set of output signals representative of electrical stimulation and/or into a second set of output signals representative of acoustic stimulation. The output signals representative of electrical stimulation are represented in FIG. 1B by arrow 115, while the output signals representative of acoustic stimulation are represented in FIG. 1B by arrow 117.

The output signals 115 are provided to the transceiver 114. The transceiver 114 is configured to use the output signals 115 to transcutaneously transfer coded signals to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the coded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the coded data and power signals are received at the transceiver 130 and provided to the stimulator unit 132. The stimulator unit 132 is configured to utilize the coded data signals to generate electrical stimulation signals (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least some residual hearing). Therefore, the cochlea of a hearing prosthesis recipient can be acoustically stimulated upon delivery of a sound signal to the recipient's outer ear. In the example of FIGS. 1A and 1B, the receiver 142 is used to aid the recipient's residual hearing. More specifically, the output signals 117 (i.e., the signals representative of acoustic stimulation) are provided to the receiver 142. The receiver 142 is configured to utilize the output signals 117 to generate the acoustic stimulation signals that are provided to the recipient. In other words, the receiver 142 is used to enhance, and/or amplify a sound signal which is delivered to the cochlea via the middle ear bones and oval window, thereby creating waves of fluid motion of the perilymph within the cochlea.

In general, the acoustic stimulation signals and the electrical stimulation signals are each generated and delivered to a recipient with a predetermined level and/or loudness in accordance with the operational map that is determined during a fitting process. In accordance with embodiments of the present invention, the electro-acoustic hearing prosthesis 100 of FIGS. 1A and 1B includes a perception monitoring module 118 that is configured to use objective measurements to detect/determine changes to a recipient's perception of sound signals and to adjust the recipient's operational map to reverse the perception changes. In particular, in response to detection of a perception change, the perception monitoring module 118 is configured to automatically adjust, in real-time, one or more operations that control the conversion of sound signals into acoustic stimulation signals and/or the electrical stimulation signals in a manner that ensures the recipient will again perceive sound signals inline with the original perceptions selected in the fitting process. Further details of the perception monitoring module 118 are provided below.

FIGS. 1A and 1B illustrate an arrangement in which the cochlear implant 100 includes an external component 102. However, it is to be appreciated that embodiments of the present invention may be implemented in hearing prostheses having alternative arrangements.

As noted above, the electro-acoustic hearing prosthesis 100 is configured to deliver both acoustic stimulation signals and electrical stimulation signals to a recipient. Acoustic stimulation combined with electrical stimulation is sometimes referred to herein as electro-acoustic stimulation. As such, the sound processor 112 is generally configured to execute sound processing and coding, defined by the recipient's operational map, to convert received sound signals into output signals that represent the acoustical or electrical stimulation signals for delivery to the recipient. The electrical stimulation signals are generated, from at least a first portion/segment (i.e., frequencies or frequency ranges) of the sound signals, while the acoustic stimulation signals are generated from at least a second portion of the sound signals. The recipient's operational map, which is determined during a fitting process, dictates how the electro-acoustic hearing prosthesis operates to convert sound signals into acoustic and/or electrical stimulation.

Also as noted above, after being fitted with an electro-acoustic hearing prosthesis, a recipient's hearing abilities can change over time which, in turn, can lead to changes in a recipient's perception of sound signals (i.e., when the recipient's hearing abilities change, the recipient's current operational map may be inadequate to represent the sound signals in a manner such that they can be properly perceived by the recipient). Sound perception changes that exist for extended periods of time can lead to undesirable negative learning outcomes. FIG. 2A illustrates operations of a hearing prosthesis, such as an electro-acoustic hearing prosthesis, to detect and remediate sound perception changes based on objective measurements in accordance with embodiments presented herein. For ease of illustration, FIG. 2A will be described with reference to electro-acoustic hearing prosthesis 100 of FIGS. 1A and 1B.

FIG. 2A is a flowchart of a method 250 which begins at 252 where the electro-acoustic hearing prosthesis 100 samples, over a period of time, the recipient's neural activity based on acoustic and electrical stimulation. More specifically, the electro-acoustic hearing prosthesis 100 delivers known electrical and/or acoustic stimulation signals, sometimes referred to herein as measurement stimulation signals, to the recipient's auditory system and records resulting inner ear potentials/responses via one or more stimulating contacts 138 and one or more amplifiers 143 (FIG. 1B) located in the implantable component 104 (i.e., integrated amplifier of the cochlear implant captures one or more windows of the evoked activity). The measured inner ear responses, which are generally represented in FIG. 1B by arrow 145, are transmitted back to the external component 102 for storage and analysis/evaluation by the perception monitoring module 118. In other words, the perception monitoring module 118 monitors the inner ear responses evoked by acoustic and/or electrical stimulation via one or more of the stimulating contacts 138.

As used herein, "inner ear responses" or "inner ear potentials" refer to any voltage potential associated with either the electrical properties of the inner ear or its physiological function and/or potentials obtained via measurements at the inner ear. Potentials of a physiological nature (i.e., potentials relating to the physiological function of the inner ear), include acoustically-evoked potentials/responses (e.g., electrocochleography (ECoG) responses) and electrically-evoked potentials/response (e.g., electrically evoked compound action potential (ECAP) responses). Other potentials of a physiological nature are referred to herein as higher evoked responses, which are potentials related to the brainstem and auditory cortex, inclusive of the electrical auditory brainstem responses (EABR), the middle latency response, and cortical responses. Potentials of a physiological nature are sometimes referred to herein as "physiological responses." Potentials of electrical nature (i.e., potentials relating to the electrical properties of the inner ear itself or intra-cochlear contacts) include voltage tomography responses, measured impedances (bulk and interface), and/or other forms of electrode (stimulating contact) voltage measurements. Potentials of electrical nature are sometimes referred to herein as "physiological electrical responses."

The neural activity is sampled over a period of time and stored within the perception monitoring module 118. The neural activity sampling may be performed, for example, periodically, at preselected times, in response to user inputs, etc. For example, the neural activity sampling may be conducted either at the start of the day or when the recipient first places the external coil 102 on his/her head. Alternatively, the neural activity sampling is conducted at times least invasive to the recipient's listening experience. In certain examples, the recipient may be provided with a notification indicating that sampling is about to be performed. Alternatively, the sampling may be conducted at sub-clinical levels that cannot be perceived by the recipient. The sampling can also be inter-dispersed with the typical operation of the hearing prosthesis such that the inner ear responses and can be obtained at a substantially regular rate.

Returning to FIG. 2A, at 254, the perception monitoring module 118 analyzes the sampled neural activity (i.e., the measured inner ear responses obtained over a period of time) to objectively determine whether the recipient is likely experiencing sound perception changes. In general, to determine whether the recipient is experiencing perception changes, the perception monitoring module 118 is configured to identify and track relative and/or absolute changes in the electrically-evoked responses and/or the acoustically-evoked responses. Sound perception changes may be detected, for example, by analyzing measured electrically-evoked responses and acoustically-evoked responses relative to one another, analyzing measured electrically-evoked responses and/or acoustically-evoked responses relative to one or more baseline responses (e.g., determined at fitting, determined based on representative recipient data, etc.).

For example, in one specific arrangement, when the electro-acoustic hearing prosthesis 100 is fit to a recipient, a particular level of electrical current produces a certain level of neural activity at a first tonotopic location, and that a particular level of acoustic stimulation produces a certain level of neural activity at a second tonotopic location. Subsequently, an analysis of electrically-evoked reveals that the level of neural activity evoked by the same particular level of electrical current is different (e.g., lower). Similarly, an analysis of acoustically-evoked responses also reveals that the particular level of acoustic stimulation produces a different level of neural activity. Given these changes, the perception monitoring module 118 determines that the recipient is likely experiencing a perception change due, for example, to changes in the recipient's residual hearing abilities.

In general, at 254 the objective measurements (i.e., inner ear responses) are used to infer a subjective quantity (i.e., the recipient's perception) and to estimate whether this subjective quantity has changed in a negative way. The reliance on objective measurements to infer the subjective quantity eliminates the need for, and reliance on, active recipient participation. This makes the determination less error prone and suitable for children, new recipients, etc.

In one form, the determination of whether the recipient is experiencing perception changes operates as a real-time pattern recognition/matching algorithm that analyzes various combinations of inner ear responses with respect to a database of known relationships between responses and perception changes. Stated differently, the inner ear responses may be used as inputs to a pattern matching algorithm that correlates various combinations of the inner ear responses with established patterns indicative of perception changes.

If it is determined at 254 that the recipient is not experiencing perception changes, then method 250 returns to 252 where the electro-acoustic hearing prosthesis 100 will continue to sample the neural activity. However, if it is determined at 254 that the recipient is likely experiencing perception changes, then method 250 proceeds to 256 where the perception monitoring module 118 determines one or more adjustments to the recipient's operational map to remediate the sound perception changes. In general, the one or more adjustments are configured so as to return the recipient's perception of sounds to as close as possible to the sound perception set during a most recent fitting process/session and, accordingly, prevent negative learning outcomes. At 258, the one or more adjustments to the recipient's operational map are implemented by the electro-acoustic hearing prosthesis 100.

Adjustments to a recipient's operational map in order to remediate the perception changes can be made in a number of different manners. In certain examples, only parameters controlling acoustic stimulation (e.g., acoustic stimulation levels) or only the parameters controlling electrical stimulation (e.g., electrical stimulation levels) are adjusted. In other embodiments, both the parameters controlling acoustic stimulation and the parameters controlling electrical stimulation are adjusted.

For example, in certain embodiments, the electro-acoustic hearing prosthesis 100 is configured to automatically adjust, in real-time, one or more operations that control the levels (e.g., amplitude) of the acoustical stimulation signals and/or the levels of the electrical stimulation signals, or automatically adjust, in real-time, one or more processing operations that control the perceptual loudness of the acoustical stimulation signals and/or the electrical stimulation signals. As a result, the perception monitoring module 118 is referred to herein as being configured to adjust the relative level and/or relative loudness of the acoustical stimulation signals to the electrical stimulation signals (i.e., adjust a ratio of the acoustical stimulation signals to the electrical stimulation signals). In one specific arrangement, the perception monitoring module 118 may be configured to adjust a "balance" between the acoustical stimulation signals and the electrical stimulation signals. As used herein, adjusting the balance between the acoustical stimulation signals and the electrical stimulation signals refers to corresponding adjustments to both the acoustical stimulation signals and the electrical stimulation signals.

It is to be appreciated that the adjustments can be made at individual acoustic and/or electrical stimulation channels or across a range of acoustic and/or electrical stimulation channels. In certain embodiments, the adjustments to the operational map may comprise a shift/change in the cross-over frequency defining the transition between acoustic and electrical stimulation.

As described further below, in certain embodiments neural activity, as indicated by inner ear responses, determined in a clinical setting may form a baseline or target defining proper sound perception. In such embodiments, the one or more adjustments are selected in order to obtain the same responses electric and/or acoustic responses, or a same balance of acoustically-evoked responses to electrically-evoked responses (i.e., effectively same neural perception across both acoustic and electrical hearing). In one form, by preserving the same balance of acoustically-evoked responses to electrically-evoked responses as in the clinical setting, negative outcomes can be minimized or reversed.

In summary, FIG. 2A illustrates techniques in accordance with embodiments presented herein where objective responses to acoustic and electrical simulation are used to detect sound perception changes resulting, for example, from residual hearing loss and to determine adjustments to the operation of the hearing prosthesis to remediate the sound perception changes. The operational adjustments allow the normalization of the cross-over regions between electrical and acoustic hearing and, accordingly, the acoustic and electrical pathways can be balanced. Stated differently, the electro-acoustic hearing prosthesis 100 operates to monitor the invoked responses to acoustic and electrical stimulation, track these responses over time, and to dynamically re-balance, in real-time, in response to identified changes, as needed. The use of both acoustically-evoked and electrically-evoked responses in combination allows the electro-acoustic hearing prosthesis 100 to compare the relative acoustic and electrical levels, and, as a result, may not be mislead by natural mutual variations due to the time of a day, drug usage, etc.

Figure 2B:
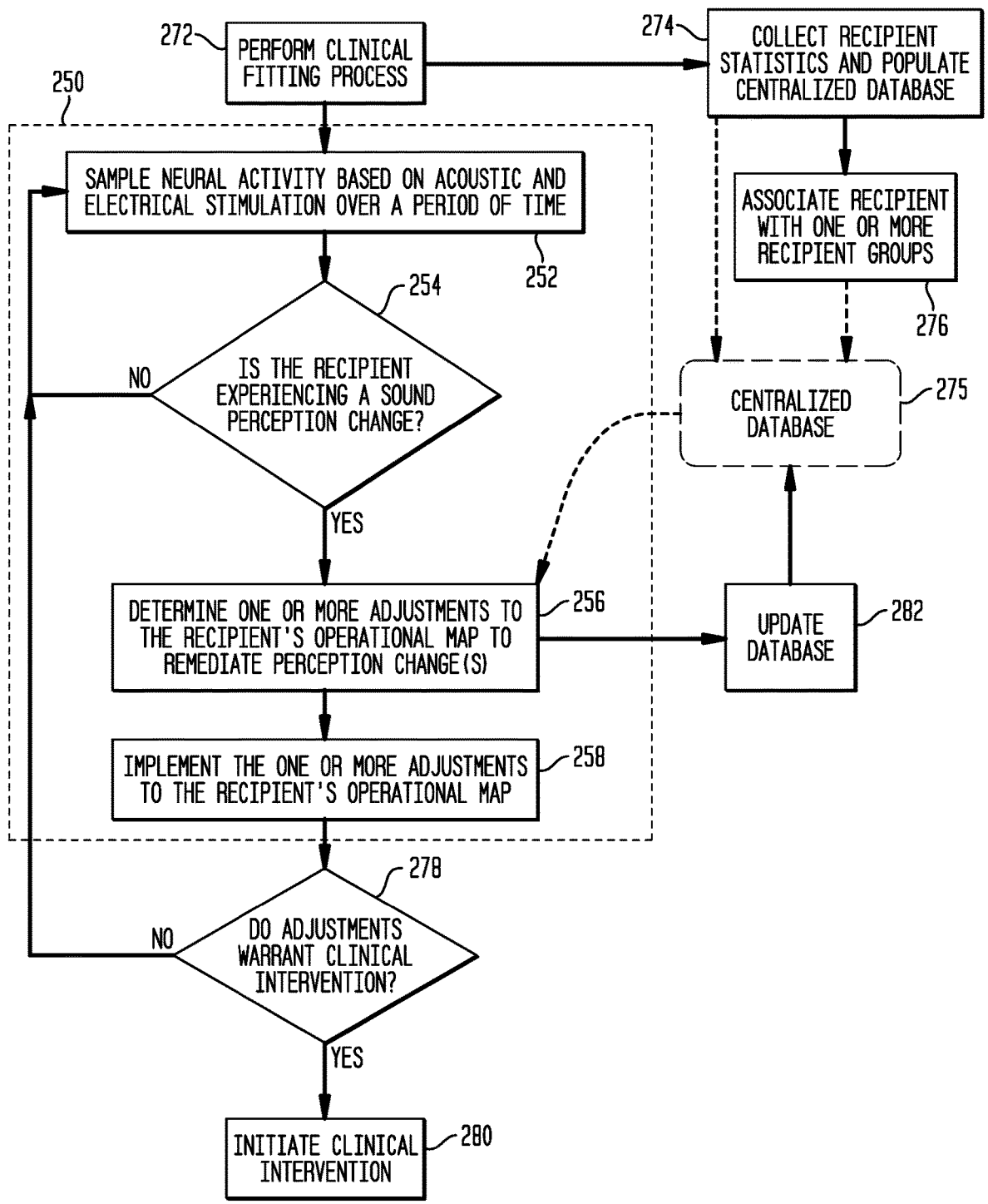
FIG. 2B is a flowchart of a method in accordance with embodiments presented herein that incorporates the method of FIG. 2A.

FIG. 2B is a flowchart illustrating method 250 of FIG. 2A implemented as part of a larger method 270. For ease of illustration, method 270 of FIG. 2B will again be described with reference to electro-acoustic hearing prosthesis 100 of FIGS. 1A and 1B.

The method 270 begins at 272 where a clinical fitting process is performed, as described above, to determine the recipient's operational map. At 274, the parameters forming the recipient's operational map, as well as recipient-specific attributes (e.g., the recipient's age, age of onset of hearing loss, type of hearing loss, etc.) are collected and stored in a centralized database 275. The centralized database 275 is a collection of data obtained from real or hypothetical recipient fitting sessions and subsequent perception monitoring sessions described herein. Within the centralized database 275, the information about different recipients may be used to form "recipient groups." Each of these recipient groups represents a subset of information that is linked in some manner, such as by operational map settings, recipient-specific attributes, etc. In one example, the centralized database 275 is part of a cloud environment.

At 276, the recipient of the electro-acoustic hearing prosthesis 100 is associated with one or more of the recipient groups based on, for example, the recipient's attributes, the recipient's clinically determined operational map settings, etc. The association between the recipient and then one or more recipient groups may also be stored in the centralized database 275.

Returning to 272, after the clinical fitting session, the clinically determined operational map is placed in use by the electro-acoustic hearing prosthesis 100 to convert sound signals into acoustic and/or electric stimulation. However, as described above, the electro-acoustic hearing prosthesis 100 also implements process 250 as described above. In particular, at 252 the electro-acoustic hearing prosthesis 100 samples, over a period of time, the recipient's neural activity based on acoustic and electrical stimulation (i.e., receives and stores inner ear responses evoked by acoustic and/or electrical stimulation via one or more of the stimulating contacts 138). As noted above, the inner ear responses may include physiological potentials, such as acoustically-evoked potentials (i.e., an ECoG response) and electrically-evoked potentials (e.g., ECAP, EABR, stapedial reflex threshold (ESRT), etc.), and/or physiological electrical potentials (e.g., EVT, impedances, etc.).

At 254 the perception monitoring module 118 analyzes the sampled neural activity to objectively determine perception changes that the recipient may be experiencing. If it is determined at 254 that the recipient is not experiencing perception changes, then the method returns to 252 where the electro-acoustic hearing prosthesis 100 will continue to sample the neural activity. However, if it is determined at 254 that the recipient is likely experiencing perception changes, then the method proceeds to 256 where the perception monitoring module 118 determines one or more adjustments to the recipient's operational map to remediate the perception changes. In the example of FIG. 2B, the determination of the one or more adjustments may optionally make use of data from the centralized database 275. For example, the perception monitoring module 118 may compare or otherwise correlate the detected changes in the inner ear responses to changes experienced by similarly situated recipients (e.g., other recipients in the recipient group or groups with which the recipient has been associated) to determine how the perception change could be effectively remediated. In certain embodiments, this correlation may also reveal other information, such as a likely cause of the perception change. As shown, at 282 the results of the one or more adjustments can be used to update the centralized database 275.

At 258, the one or more adjustments to the recipient's operational map are implemented by the electro-acoustic hearing prosthesis 100. At 278, a determination is made as whether or not the adjustments warrant clinical intervention (i.e., are the adjustments excessive/significant). If it is determined at 278 that the one or more adjustments do not warrant clinical intervention, then the method returns to 252. However, if it is determined at 278 that the one or more adjustments are sufficient to warrant clinical intervention, the electro-acoustic hearing prosthesis 100 may initiate the clinical intervention at 280. The electro-acoustic hearing prosthesis 100 may initiate the clinical intervention by, for example, generating an audible or visible notification to the recipient via the sound processing unit or some associated device, sending a notification to a clinic or other external party, etc.

Although FIG. 2B illustrates the operations of 278 and 280 occurring after the operations of 258, it is to be appreciated that this is merely illustrative and that the determination of 278 could be performed before implementing the one or more adjustments. In such embodiments, the electro-acoustic hearing prosthesis 100 may continue to operate using the prior operational map until the recipient is able to receive the clinical intervention.

Figure 3A:
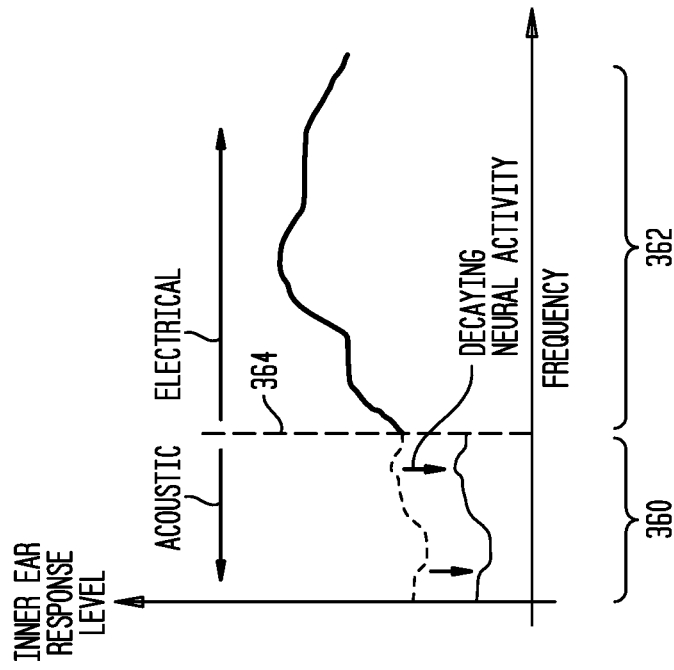
FIGS. 3A and 3B are graphs that collectively illustrate inner ear response changes that cause a recipient to experience a perception change.
Figure 3B:
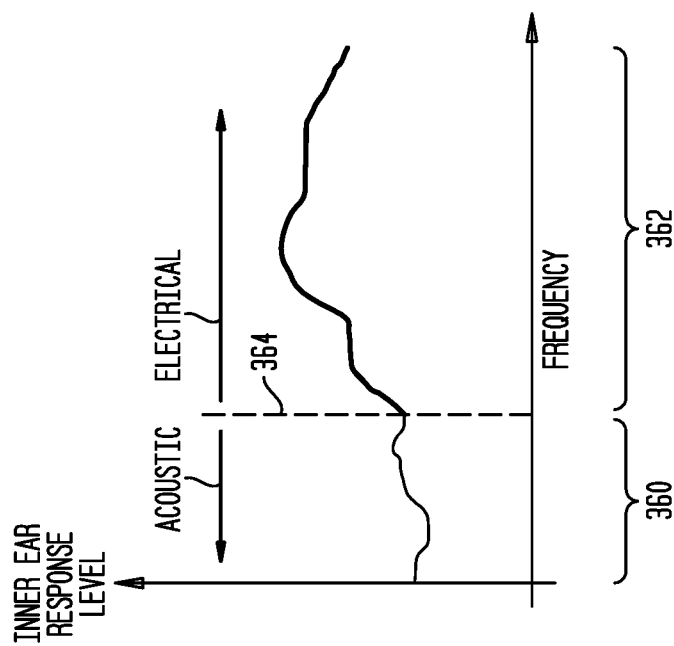

FIGS. 3A, 3B, 4A, and 4B illustrate specific example applications of the techniques presented herein. Referring first to FIGS. 3A and 3B, shown are graphs that each have a vertical (Y) axis representing increasing inner ear response levels, and a horizontal (X) axis representing increasing frequency. Each of the graphs in FIGS. 3A and 3B also includes a first section 360 that corresponds to acoustic stimulation, and a second section 362 that corresponds to electrical stimulation. That is, section 360 generally represents the levels of inner ear responses and frequencies associated with the acoustic stimulation signals, while section 362 generally represents the levels of inner ear responses and frequencies associated with the electrical stimulation signals. As noted above, acoustic and electrical stimulation may evoke different types of inner ear responses that have different "levels." However, for ease of illustration, the acoustically-evoked inner response levels and the electrically-evoked inner ear response levels have been normalized for collective representation by the vertical axis in FIGS. 3A and 3B.

FIG. 3A illustrates levels of inner ear responses, for respective frequencies, that are determined in a clinical (e.g., initial) fitting process. That is, as noted above, an operational map is clinically determined for a recipient. This operational map is used by the electro-acoustic hearing prosthesis 100 to convert sound signals of a given frequency to stimulation (either acoustic or electrical), which then evokes the levels of inner ear responses shown in FIG. 3A. FIG. 3A also schematically illustrates a cross-over frequency 364 where the stimulation transitions from acoustic to electrical stimulation (i.e., the divide between sections 360 and 362). Merely for ease of illustration, the cross-over frequency 364 is shown as a discrete point where acoustic stimulation ends and electrical stimulation begins. However, it is to be appreciated that, in practice, acoustic and electrical stimulation may overlap within a range of frequencies at or near the cross-over frequency 364.

As described above with reference to FIGS. 2A and 2B, over a period of time the electro-acoustic hearing prosthesis 100 samples the recipient's neural activity in response to acoustic and electrical stimulation and determines whether the recipient is likely experiencing perception changes. FIG. 3B illustrates an example in which the electro-acoustic hearing prosthesis 100 determines that the recipient is likely experiencing perception changes due to a decay in the neural activity across a range of acoustic frequencies (i.e., across the tonotopic region of the cochlea associated with acoustic hearing). That is, as shown in section 360 of FIG. 3B, the levels of the inner ear responses measured by the electro-acoustic hearing prosthesis 100 drop across the entirety of the acoustic hearing frequency range.

In one example, the decay in the neural activity within the acoustic region indicates that the recipient's residual hearing has declined, either permanently or temporarily, due to, for example, disease, trauma, etc. As such, the electro-acoustic hearing prosthesis 100 detects over a period of time (e.g., several days, weeks, or months) that the inner ear responses generated in response to acoustic stimulation have decayed relative to those obtained in response to electrical stimulation. For example, at fitting, an input sound pressure level (SPL) of 20 dB-HL delivered at the 3 kHz region produces a neural response at 40 uV, while acoustic stimulation delivered at the 1 kHz region at the same sound input level of 20 dB-HL produces a neural response at 20 uV. The electro-acoustic hearing prosthesis 100 detects that the neural response activity evoked by the acoustic stimulation at the 20 dB-HL input level delivered at the 1 kHz region has dropped relative to the neural response activity being produced by the electrical stimulation at the 20 dB-HL delivered at the 3 kHz region.

Based on the above change in the relative levels of the acoustically-evoked and electrically-evoked inner ear responses, the electro-acoustic hearing prosthesis 100 determines that the recipient is likely experiencing a perception change. The electro-acoustic hearing prosthesis 100 may then make adjustments to the recipient's operational map to remediate the perception change. In one embodiment, the electro-acoustic hearing prosthesis 100 compensates by increasing the gain applied to the acoustic channels to re-balance the neural response levels. The electro-acoustic hearing prosthesis 100 may also notify/alert a clinician/audiologist of the changes.

As noted above, in certain embodiments, the electro-acoustic hearing prosthesis 100 compares measured inner ear responses with a centralized database in order to classify the observed trends against known patterns/recipient groups. In general, the electro-acoustic hearing prosthesis 100 operates to prevent negative learning outcomes during this time, whereby the brain becomes attuned to hearing without the fill content of the lower frequencies (i.e., prevent the brain from training itself not use the content at these frequencies, which would limit future learning outcomes).

In the example of FIG. 3B, the electro-acoustic hearing prosthesis 100 continues to monitor the inner ear responses. The acoustically-evoked responses may permanently decline or, in certain cases, may improve and return to the prior levels (e.g., recovery from an illness).

Figure 4B:
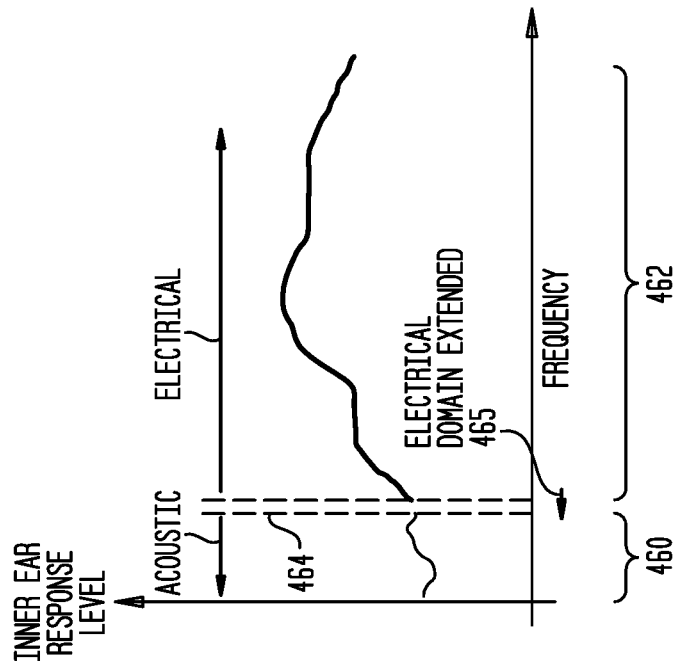
FIGS. 4A and 4B are graphs that collectively illustrate inner ear response changes that cause a recipient to experience a perception change.
Figure 4A:
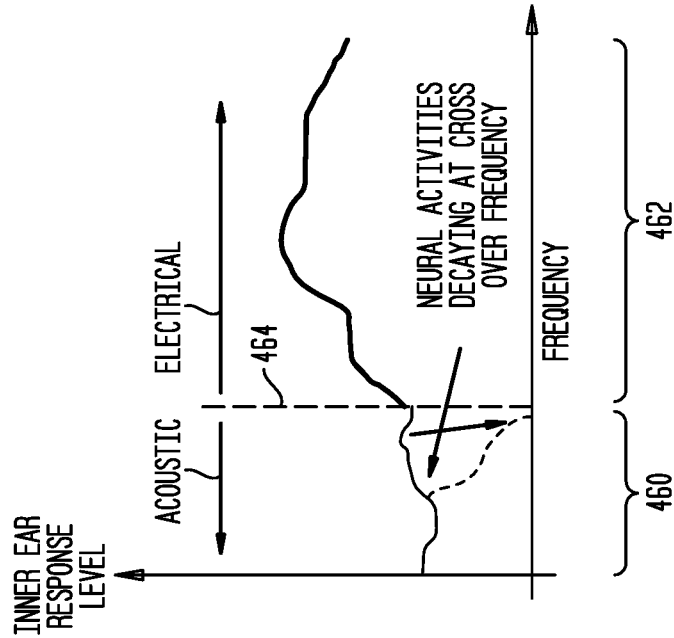

Referring next to FIGS. 4A and 4B, shown are graphs that each has a vertical (Y) axis representing increasing inner ear response levels, and a horizontal (X) axis representing increasing frequency. The graphs in FIGS. 4A and 4B also include a first section 460 that corresponds to acoustic stimulation, and a second section 462 that corresponds to electrical stimulation. Similar to FIGS. 3A and 3B, for ease of illustration the acoustically-evoked inner response levels and the electrically-evoked inner ear response levels have been normalized for collective representation by the vertical axis in FIGS. 4A and 4B.

As described above with reference to FIGS. 2A and 2B, over a period of time the electro-acoustic hearing prosthesis 100 samples the recipient's neural activity in response to acoustic and electrical stimulation and determines whether the recipient is likely experiencing perception changes. FIG. 4A illustrates an example in which the electro-acoustic hearing prosthesis 100 determines that a recipient is likely experiencing perception changes due to a significant drop in neural activity evoked in response to acoustic stimulation just below the cross-over frequency 464 (i.e., the divide between acoustic and electrical stimulation).

For example, as shown in FIG. 4A, the neural response activity begins to drop significantly at 2 kHz, but is normal at lower acoustic frequencies. The electro-acoustic hearing prosthesis 100 then makes adjustments to the recipient's operational map to remediate the perception change or changes. In one embodiment, the electro-acoustic hearing prosthesis 100 compensates by re-organizing the frequency bands so that the frequencies at which the neural response has dropped will be covered by electrical stimulation. That is, as shown by arrow 465 in FIG. 4B, the electro-acoustic hearing prosthesis 100 adjusts the recipient's operational map to shift the cross-over frequency 464 lower, thereby lengthening the tonotopic region covered by electrical stimulation and shortening the tonotopic region covered by acoustic stimulation. This downward shift in the cross-over frequency 464 prevents the recipient from experiencing a gap in his/her frequency perception which, over time, can result in negative learning outcomes.

It is to be appreciated that the examples of FIGS. 3A-3B and 4A-4B are merely illustrative and that the techniques presented herein may detect a number of different types of perception changes and make a number of different types of adjustments. For example, in one alternative example, the electrically-evoked inner ear response levels may fluctuate differently from the acoustically-evoked levels due to, for example, tissue hardening (e.g., the electro-acoustic hearing prosthesis 100 detects a reduction in the electrically-evoked inner ear response levels). In one such embodiment, the electro-acoustic hearing prosthesis 100 adjusts the recipient's operational map to increase the electrical stimulation current levels. In certain embodiments, the electro-acoustic hearing prosthesis 100 may query a centralized database regarding, for example, the age of implementation of the recipient to determine whether the neural activity behavior is normal/expected. This information can be used in different manners, including in selection of the adjustments to the recipient's operational map.

In another example, the recipient may suffer from a disease/illness that causes increased sensitivity in the acoustic region (i.e., increased levels of acoustically-evoked inner ear responses). When the electro-acoustic hearing prosthesis 100 detects an increase in the acoustically-evoked inner ear responses relative to the electrically-evoked responses, the electro-acoustic hearing prosthesis 100 may query a centralized database to see if the measured inner ear responses can be correlated to any known disease. If this query is successful (i.e. correlates the recipient's measured inner ear responses with a known disease), the query may also return a strategy for adjustments to the recipient's operational map. This strategy may be developed based on adjustments made for other recipients experiencing the same disease and, possibly, sharing common attributes (e.g., age, type of deafness, etc.) with the recipient. In one embodiment, the electro-acoustic hearing prosthesis 100 temporarily reduces the acoustic stimulation level, monitors the situation, and notifies a hearing professional or other medical practitioner of the possible occurrence and affects of the disease.

In yet another example, the electro-acoustic hearing prosthesis 100 detects an increase in the level of acoustically-evoked inner ear responses relative to the electrically-evoked responses, and the electro-acoustic hearing prosthesis 100 queries a centralized database to determine if the measured inner ear responses can be correlated to any known disease. However, in this example, the measured inner response trends cannot be correlated to any known behavior and the electro-acoustic hearing prosthesis 100 or other entity (e.g., a centralized system) notifies a medical practitioner. In certain embodiments, the medical practitioner analyses the trend/pattern, makes a diagnosis, and selects an operational map adjustment strategy. If/when the operational map adjustment strategy is validated, the strategy can then be uploaded into the centralized database for subsequent use by other prostheses, clinics, etc.

The above examples have been primarily described with reference to determination of perception changes and selection of operational map adjustments based on the "levels" of inner ear responses. It is to be appreciated that use of the inner ear response levels in the above examples is illustrative and that the techniques presented herein may make use of various attributes of inner ear responses to determine perception changes and/or to selection operational map adjustments to remediate perception changes. For example, in accordance with embodiments presented herein, these determinations can be made based not only on the levels (i.e., magnitude/amplitude), but also or alternatively on the phase, shape of the responses (morphology), frequency, indirect user feedback, or other aspects of the responses. In certain examples, a system that observes auditory environmental composition, and correlates a user-induced reduction in volume when the environment is dominated by low frequency content may be used an indicator of increased sensitivity to low frequency (acoustical) stimulation.

Figure 5:
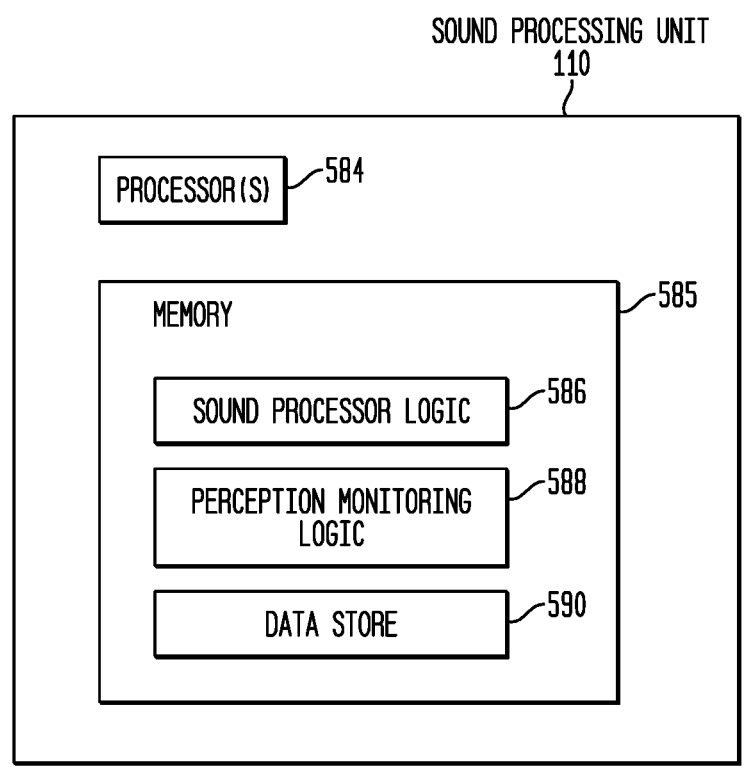
FIG. 5 is a block diagram of a sound processing unit of an electro-acoustic hearing prosthesis in accordance with embodiments presented herein.

FIG. 5 is a schematic block diagram illustrating an arrangement for a sound processing unit, such as sound processing unit 110, in accordance with an embodiment of the present invention. As shown, the sound processing unit 110 includes one or more processors 584 and a memory 585. The memory 585 includes sound processor logic 586, perception monitoring logic 588, and a data store 590.

The memory 585 may be read only memory (ROM), random access memory (RAM), or another type of physical/tangible memory storage device. Thus, in general, the memory 585 may comprise one or more tangible (non-transitory) computer readable storage media (e.g., a memory device) encoded with software comprising computer executable instructions and when the software is executed (by the one or more processors 584) it is operable to perform the operations described herein with reference to the sound processor 112 and the perception monitoring module 118.

FIG. 5 illustrates software implementations for the sound processor 112 and the perception monitoring module 118. However, it is to be appreciated that one or more operations associated with the sound processor 112 and the perception monitoring module 118 may be partially or fully implemented with digital logic gates in one or more application-specific integrated circuits (ASICs).

Merely for ease of illustration, the perception monitoring module 118 has been shown and described as elements that are separate from the sound processor 112. It is to be appreciated that the functionality of the perception monitoring module 118 may be incorporated into the sound processor 112.

As detailed above, embodiments presented herein are directed to techniques enabling an electro-acoustic or other type of hearing prosthesis to objectively determine that a recipient is experiencing changes to how he/she is perceiving sounds (perception changes). The use of objective measurements, rather than subjective measurements, to detect perception changes does not require the recipient to actively participate in the detection of the perception change. Once one or more perception changes are detected, the electro-acoustic hearing prosthesis may immediately initiate one or more corrective actions to address the perception changes. As described above, the one or more corrective actions may include adjustments to the recipient's operational map to reverse the one or more perception changes in order to prevent negative learning outcomes. The techniques presented herein may, for example, provide developmental benefits, physiological benefits, assist in disease identification and understanding, etc.

As noted, embodiments of the present invention have been described herein with reference to one specific type of hearing prosthesis, namely an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A hearing prosthesis, comprising:
an intra-cochlear stimulating assembly configured to be implanted in a recipient, wherein the intra-cochlear stimulating assembly comprises a plurality of stimulating contacts configured to deliver electrical stimulation signals to the recipient; and
one or more processors configured to:
obtaining inner ear responses evoked by one or more electrical stimulation signals or acoustic stimulation signals delivered via an acoustic receiver;
objectively identifying, based on an analysis of the obtained inner ear responses, one or more changes in the recipient's perception of sound signals relative to a predetermined perception of sound signals; and
adjusting one or more operations of the hearing prosthesis to reverse the one or more changes in a recipient's perception of sound signals.

2. The hearing prosthesis of claim 1, wherein the hearing prosthesis is an electro-acoustic hearing prosthesis configured to deliver the acoustic stimulation signals and the electrical stimulation signals to the recipient.

3. The hearing prosthesis of claim 2, wherein to adjust one or more operations of the hearing prosthesis to remediate the perception change, the one or more processors are configured to:
adjust a ratio of acoustic stimulation signals used to evoke perception of sound signals relative to electrical stimulation signals used to evoke perception of sound signals.

4. The hearing prosthesis of claim 3, wherein to adjust a ratio of the acoustic stimulation signals to the electrical stimulation signals, the one or more processors are configured to:
adjust a level of the acoustic stimulation signals relative to a level of the electrical stimulation signals.

5. The hearing prosthesis of claim 3, wherein to adjust a ratio of the acoustic stimulation signals to the electrical stimulation signals, the one or more processors are configured to:

adjust a perceptual loudness of the acoustic stimulation signals relative to a perceptual loudness of the electrical stimulation signals.

6. The hearing prosthesis of claim 3, wherein to adjust one or more operations of the hearing prosthesis to remediate the perception change, the one or more processors are configured to:

adjust a cross-over frequency at which the electro-acoustic hearing prosthesis transitions from delivery of acoustic stimulation signals to delivery of electrical stimulation signals.

7. The hearing prosthesis of claim 1, wherein to adjust one or more operations of the hearing prosthesis to remediate the perception changes, the one or more processors are configured to:

correlate the inner ear responses with predetermined neural activity that is specific for the recipient.

8. The hearing prosthesis of claim 1, wherein to obtain inner ear responses evoked by stimulation signals, the one or more processors are configured to:

obtain a plurality of acoustically-evoked responses and a plurality of electrically-evoked responses over a period of time.

9. A method, comprising:

at a hearing prosthesis worn by a recipient, obtaining inner ear responses evoked by stimulation signals;

objectively identifying, based on an analysis of the obtained inner ear responses, one or more changes in the recipient's perception of sound signals relative to a predetermined perception of sound signals; and adjusting operation of the hearing prosthesis to reverse the one or more changes in a recipient's perception of sound signals.

10. The method of claim 9, wherein the hearing prosthesis is an electro-acoustic hearing prosthesis configured to deliver acoustic stimulation signals and electrical stimulation signals to the recipient.

11. The method of claim 10, wherein adjusting one or more operations of the hearing prosthesis to remediate the perception change comprises:

adjusting a ratio of acoustic stimulation signals used to evoke perception of sound signals relative to electrical stimulation signals used to evoke perception of sound signals.

12. The method of claim 11, wherein adjusting a ratio of the acoustic stimulation signals to the electrical stimulation signals comprises:

adjusting a level of the acoustic stimulation signals relative to a level of the electrical stimulation signals.

13. The method of claim 11, wherein adjusting a ratio of the acoustic stimulation signals to the electrical stimulation signals comprises:

adjusting a perceptual loudness of the acoustic stimulation signals relative to a perceptual loudness of the electrical stimulation signals.

14. The method of claim 10, wherein adjusting one or more operations of the hearing prosthesis to remediate the perception change comprises:

adjusting a cross-over frequency at which the electro-acoustic hearing prosthesis transitions from delivery of acoustic stimulation signals to delivery of electrical stimulation signals.

15. The method of claim 9, wherein adjusting operation of the hearing prosthesis to remediate the perception changes includes:

correlating the inner ear responses with predetermined neural activity that is specific for the recipient.

16. The method of claim 9, wherein obtaining inner ear responses evoked by stimulation signals comprises:

obtaining a plurality of acoustically-evoked responses and a plurality of electrically-evoked responses over a period of time.

17. A hearing prosthesis, comprising:

an intra-cochlear stimulating assembly configured to be implanted in a recipient, wherein the intra-cochlear stimulating assembly comprises a plurality of stimulating contacts configured to deliver electrical stimulation signals to the recipient; and one or more processors configured to:

sample, via one or more of the stimulating contacts, neural activity of the recipient in response to measurement stimulation signals, analyze the sampled neural activity to determine that the recipient has experienced a sound perception change, and adjust, based on the sound perception change experienced by the recipient, one or more settings of the hearing prosthesis used to convert sound signals into acoustic stimulation signals or electrical stimulation signals, wherein the one or more settings are adjusted to restore a sound perception of the recipient to a predetermined sound perception.

18. The hearing prosthesis of claim 17, wherein the intra-cochlear stimulating assembly and the one or more processors are part of an implantable component of the hearing prosthesis.

19. The hearing prosthesis of claim 17, wherein to adjust one or more settings of the hearing prosthesis, the one or more processors are configured to:

adjust at least one of a level or a perceptual loudness of the acoustic stimulation signals relative to the electrical stimulation signals.

20. The hearing prosthesis of claim 17, wherein to adjust one or more settings of the hearing prosthesis, the one or more processors are configured to:

adjust a cross-over frequency at which the hearing prosthesis transitions from delivery of acoustic stimulation signals to delivery of electrical stimulation signals.

* * * * *